US00PP27582P3

(12) United States Plant Patent
Adams

(10) Patent No.: US PP27,582 P3
(45) Date of Patent: Jan. 24, 2017

(54) RASPBERRY PLANT NAMED 'BOUNTIFUL'

(50) Latin Name: *Rubus idaeus*
Varietal Denomination: BOUNTIFUL

(71) Applicant: PLANT SCIENCES, INC., Watsonville, CA (US)

(72) Inventor: Scott W. Adams, Watsonville, CA (US)

(73) Assignee: Plant Sciences, Inc., Watsonville, CA (US)

( * ) Notice: Subject to any disclaimer, the term of this patent is extended or adjusted under 35 U.S.C. 154(b) by 177 days.

(21) Appl. No.: 14/121,207

(22) Filed: Aug. 12, 2014

(65) Prior Publication Data

US 2016/0050823 P1 Feb. 18, 2016

(51) Int. Cl.
*A01H 5/08* (2006.01)

(52) U.S. Cl.
USPC ..... Plt./204

(58) Field of Classification Search
USPC ..... Plt./204
See application file for complete search history.

*Primary Examiner* — Keith Robinson
(74) *Attorney, Agent, or Firm* — Foley & Lardner LLP

(57) ABSTRACT

This invention relates to a new and distinct everbearing variety of raspberry plant named 'BOUNTIFUL'. The new variety is primarily adapted to the growing conditions of the central coast of California and is characterized by the following: late primocane production with medium sized fruit of light-red coloration. Fruit is of consistent conic shape, releases very easily from the receptacle and is of good flavor. Foliage is flat to slightly concave, medium green; possessing weak rugosity and equal 3-5 foliates. Primocanes have an absent or very weak waxy coat, medium to dense thorn density and no anthocyanin coloration.

4 Drawing Sheets

Latin name of the genus and species of the plant clamed: *Rubus idaeus.*

Variety denomination: 'BOUNTIFUL'.

BACKGROUND OF THE INVENTION

The present invention relates to a new and distinct fall bearing raspberry variety designated as 'BOUNTIFUL'. This new variety is a result of a controlled cross made in 2007 in Watsonville, Calif. between raspberry variety 'ELEGANCE' (patented, U.S. Plant Pat. No. 21,685) as the female parent and raspberry variety 'PS-3636' (unpatented) as the male parent in an ongoing breeding program. The variety is botanically known as *Rubus idaeus.*

The seedling resulting from the aforementioned cross was asexually propagated by dormant canes in Santa Cruz County, Calif. and was subsequently selected by the inventor from a controlled breeding plot in Watsonville, Calif. in 2009. After its selection, the new variety was further asexually propagated by dormant canes, roots and non-dormant root shoot cuttings in Santa Cruz County, Calif., San Joaquin County, Calif. and Siskiyou County, Calif. The new variety was then extensively tested over the next several years in fruiting fields in Santa Cruz County, Calif. This propagation has demonstrated that the combination of traits disclosed herein as characterizing the new variety are fixed and remain true to type through successive generations of asexual reproduction.

BRIEF SUMMARY OF THE INVENTION

'BOUNTIFUL' is primarily adapted to the climate and growing conditions of the central coast of California. This region provides the necessary year-round temperatures required for it to produce and maintain a strong vigorous plant and to remain in fruit production from July through December on primocanes and in the ensuing year from May through July on the floricanes. The following traits have been repeatedly observed and are determined to be unique characteristics of 'BOUNTIFUL', which in combination distinguish this raspberry plant as a new and distinct variety:

1. Late primocane fruiting
2. Very high fruit yield
3. Light fruit color
4. Very weak adherence of receptacle
5. Good flavor The raspberry variety that is believed to be most closely related to the new raspberry variety 'BOUNTIFUL' is the raspberry variety 'GRANDEUR' (patented, U.S. Plant Pat. No. 20,459). In comparison to the similar raspberry variety 'GRANDEUR', 'BOUNTIFUL' differs by the following combination of characteristics described in Table 1:

TABLE 1

| Characteristic | 'BOUNTIFUL' | 'GRANDEUR' (US PP20,459) |
|---|---|---|
| Primocane waxy coat (glaucosity) | Absent to very weak | Absent to very weak |
| Predominate number of leaflets | Equal 3-5 | Always 3 |
| Leaf shape (cross section) | Flat to slightly concave | Flat to slightly convex |
| Rugosity | Weak | Strong |
| Color mature fruit | RHS 34A<br>Light red | RHS 42A<br>Medium red |
| Primocane fruit weight (g) | 4.8 | 3.9 |
| Floricane color | RHS 165B<br>Greyed-orange group | RHS 164A<br>Greyed-orange group |

'BOUNTIFUL' differs from its parents, 'ELEGANCE' and 'PS-3636' by the following combination of characteristics described in Table 2:

TABLE 2

| Characteristic | 'BOUNTIFUL' | 'ELEGANCE' (U.S. Plant Pat. No. 21,685) | 'PS-3636' |
|---|---|---|---|
| Productivity | Very high | Medium to low | Medium |
| Glossiness (fruit) | Medium | High | Medium |
| Adherence of receptacle | Very weak | Medium | Medium |
| Primocane time of fruiting | Late | Late | Late |
| Fruit size | Medium | Small | Medium |
| Flavor | Good | Good | Poor |

For identification, a series of molecular markers have been determined for this new variety.

BRIEF DESCRIPTIONS OF THE DRAWINGS

The accompanying color photographs illustrate the overall appearance of typical specimens of the new raspberry variety, 'BOUNTIFUL' at various stages of development as true as reasonably possible with color reproductions of this type. Color in the photographs may differ slightly from the color value cited in the detailed botanical description which accurately describes the color of 'BOUNTIFUL'. The depicted plant and plant parts of the new raspberry variety 'BOUNTIFUL' were taken in Watsonville, Calif. and are approximately 2 to 16 months old:

DETAILED BOTANICAL DESCRIPTION

Figure 1:
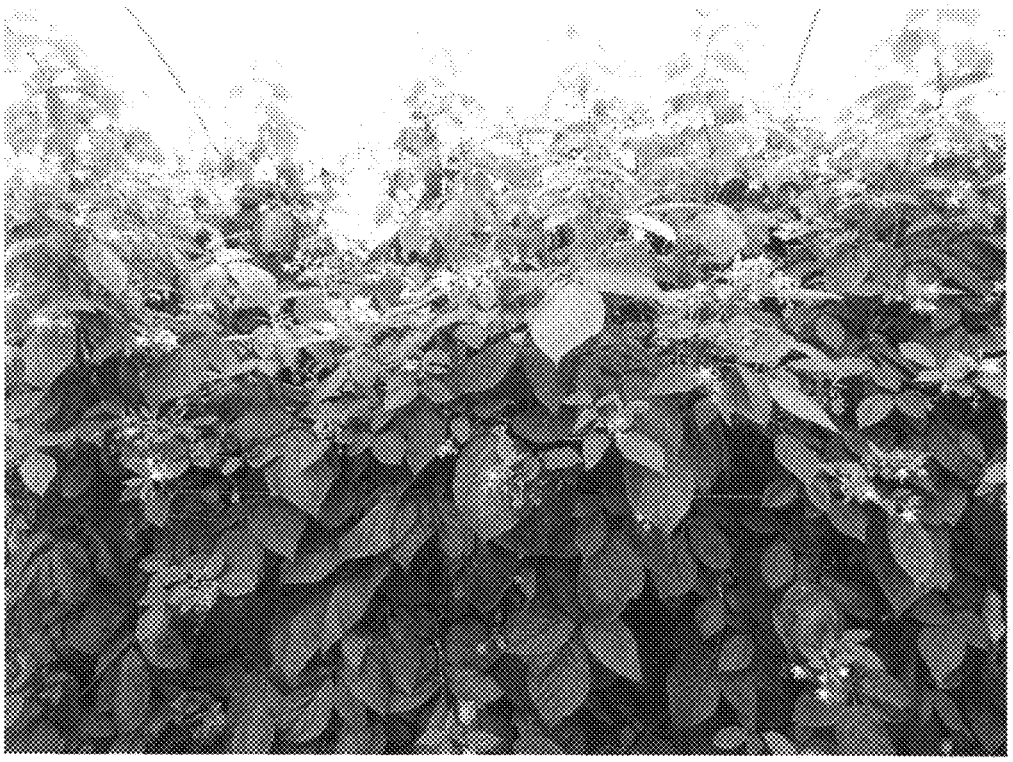
FIG. 1 shows typical primocane foliage and fruit color; foliate and rugosity characteristics of 'BOUNTIFUL' taken in the month of July 2014.
Figure 2:
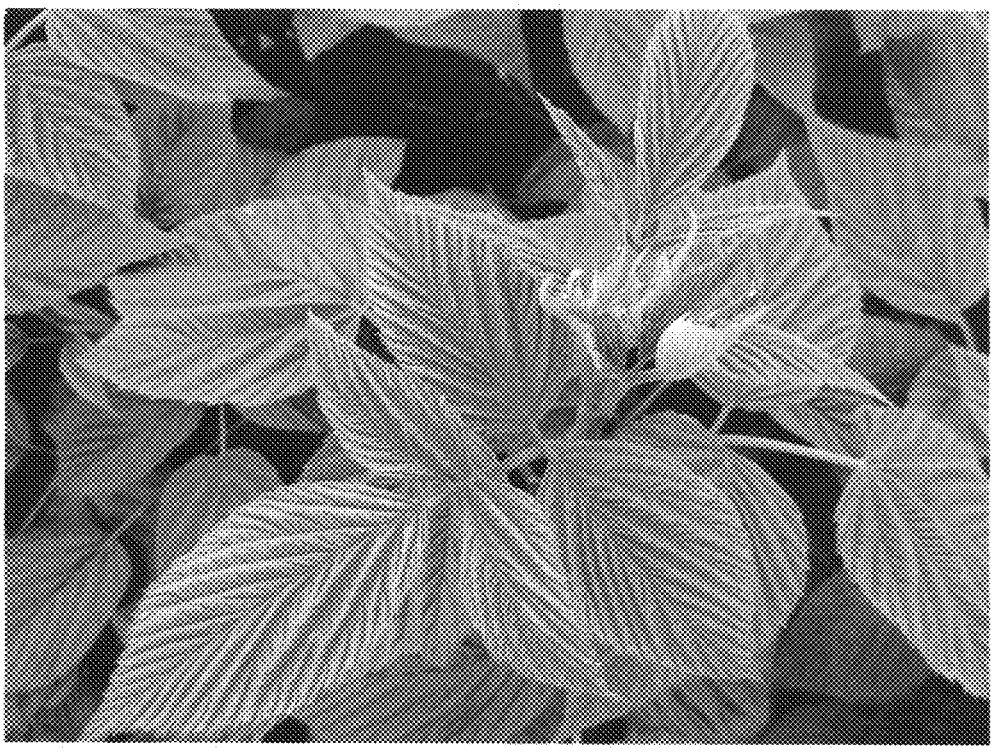
FIG. 2 shows typical coloration of apical growing tip during early primocane rapid growth of 'BOUNTIFUL' taken in the month of May 2013.
Figure 3:
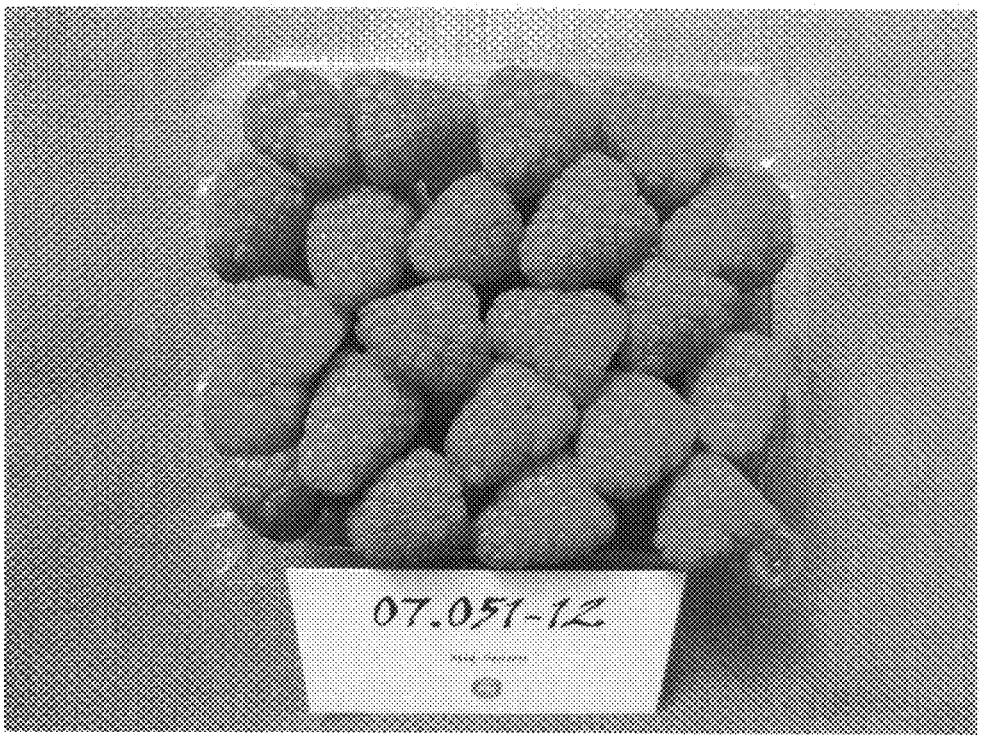
FIG. 3 shows typical harvested fruit of 'BOUNTIFUL' taken in the month of August 2013.
Figure 4:
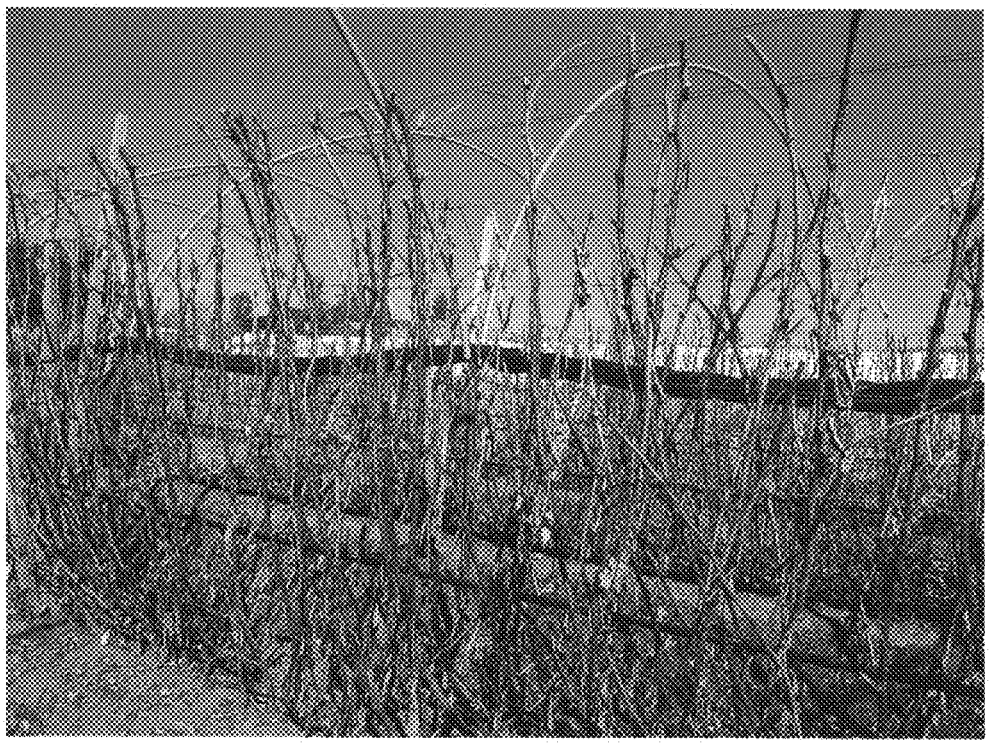
FIG. 4 shows typical dormant cane color characteristics of 'BOUNTIFUL' taken in the month of January 2013.

'BOUNTIFUL' has not been observed under all possible environmental conditions. The characteristics of the new variety may vary in detail, depending upon variations in environmental factors, including weather (temperature, humidity and light intensity), day length, soil type, and location.

The aforementioned photographs, together with the following description of the new raspberry variety 'BOUNTIFUL', unless otherwise noted, are based upon observations taken during the 2013-2014 growing season in Watsonville, Calif. Primocane measurements and ratings were taken from plants of 'BOUNTIFUL' dug from a nursery located in Siskiyou County, Calif. during the middle of October 2012 and planted approximately 3 to 4 weeks later in Watsonville, Calif. The approximate age of the observed primocane plants is 7 to 8 months. Floricane measurements and ratings were taken from the same planting of 'BOUNTIFUL' at an approximate age of 16 to 18 months. Yield observations and fruit quality characteristics are averaged from five years of data collected from the 2009 through 2013 production seasons. Flower measurements and characteristics are from secondary flowers unless otherwise noted. Fruit characteristics and measurements are from secondary fruit unless otherwise noted. Foliage characteristics and measurements are from 3-foliate foliage unless otherwise noted.

Color terminology where noted follows The R.H.S. Colour Chart Fifth Edition, Royal Horticultural Society, London, United Kingdom (1966).

The following tables 3-7 describe fruit, plant, foliage, flower and pest/disease characteristics of the new raspberry 'BOUNTIFUL' in comparison to the similar raspberry varieties 'GRANDEUR' (patented, U.S. Plant Pat. No. 20,459).

TABLE 3

FRUIT CHARACTERISTICS

| Characteristic | 'BOUNTIFUL' | 'GRANDEUR' (U.S. Plant Pat. No. 20,459) |
|---|---|---|
| Color mature fruit | RHS 34A<br>Light to medium red | RHS 42A<br>Medium red |
| Color achenes | RHS 159A<br>Orange-white group | RHS 159A<br>Orange-white group |
| Fruit length (mm) | 23.30 | 22.91 |
| Fruit width (mm) | 21.87 | 20.12 |
| Length/Width ratio | 1.06<br>Longer than broad | 1.14<br>Longer than broad |
| Seed weight (mg) | 1.66 | 1.75 |
| Druplets per berry | 82 | 93 |
| Weight of single drupe (g/drupe) | 0.058 | 0.043 |
| Relative size of drupes | Medium | Medium |
| Fruit size | Medium | Medium |
| Predominant shape | Conical | Conical |
| Evenness of color | Even | Even |
| Glossiness | Medium | Medium |
| Adherence of receptacle | Very weak | Weak |
| Firmness of flesh | Firm | Very firm |
| Firmness of skin | Medium | Very firm |
| Soluble Solids (% brix) | 9.8 | 10.5 |
| Flavor | Good | Good |

TABLE 4

PLANT CHARACTERISTICS

| Characteristic | 'BOUNTIFUL' | 'GRANDEUR' (U.S. Plant Pat. No. 20,459) |
|---|---|---|
| General: | | |
| Habit | Semi-upright | Upright |
| Size | Medium | Medium |
| Productivity | High | High |
| Self-fruitfulness | Yes | Yes |
| Type of bearing | Everbearing | Everbearing |
| Primocane: | | |
| Color (true) | RHS 145B<br>Yellow-green group | RHS 145B<br>Yellow-green group |
| Length (cm) | 198.6 | 143.6 |
| Basal diameter (mm) | 16.98 | 21.80 |
| Diameter central ⅓ (mm) | 10.31 | 12.55 |
| Lateral length at central ⅓ (cm) | 35.2 | 43.6 |
| No. fruiting laterals per cane | 15.2 | 17.4 |
| Internode length at central ⅓ (mm) | 50.34 | 48.84 |
| Anthocyanin coloration | n/a | RHS 59B<br>Red-purple group |
| Anthocyanin intensity | Absent | Weak |
| Pubescence | Absent | Absent |
| Length of vegetative bud (mm) | 6.82 | 11.01 |

TABLE 4-continued

| PLANT CHARACTERISTICS | | |
|---|---|---|
| Characteristic | 'BOUNTIFUL' | 'GRANDEUR' (U.S. Plant Pat. No. 20,459) |
| Strength of waxy coat (glaucosity) | Absent to very weak | Absent to very weak |
| Time of flowering | Late | Medium |
| Time of fruiting | Late | Medium |
| Length of fruiting season | Long | Long |
| % of total yield | 47% | 50% |
| Flowering period | Late June to Late November | Late June to Late November |
| Harvest period | Late July to Late December | Late July to Late December |
| Primocane fruit weight (g) | 4.8 | 3.9 |
| Primocane yield (g/plant) | 3,495 | 2,662 |
| Young Shoots: | | |
| Number (per meter) | 25-30 | 15-20 |
| | Medium | Medium |
| Anthocyanin presence | Present | Present |
| Anthocyanin coloration | RHS 179B Red-purple group | RHS 179A Greyed-red group |
| Anthocyanin intensity | Absent to very weak | Medium |
| Thorns: | | |
| Thorn coloration | RHS 179C Greyed-red group | RHS 180C Greyed-red group |
| Thorn length at central ⅓ (mm) | 1.92 | 0.76 |
| Thorn base at central ⅓ (mm) | 1.34 | 1.53 |
| Thorn presence | Present | Present |
| Thorn density per cm at central ⅓ | 7.36 | 3.38 |
| | Dense | Medium |
| Thorn texture | Rigid | Rigid |
| Attitude of the tip | Horizontal | Horizontal |
| Floricane: | | |
| Color (true) | RHS 165B Greyed-orange group | RHS 164A Greyed-orange group |
| Length (cm) | 139.7 | 119.8 |
| Fruiting lateral attitude | Horizontal to drooping | Erect |
| Time bud burst | Medium | Medium |
| Time of flowering | Medium | Medium |
| Time of fruiting | Medium | Medium |
| Length of fruiting season | Medium to long | Medium to long |
| % of total yield | 53% | 50% |
| Flowering period | Late April to Late June | Late April to Late June |
| Harvest period | Late May to Late July | Late May to Late July |
| Floricane fruit weight (g) | 4.6 | 3.7 |
| Floricane yield (g/plant) | 4,010 | 2,680 |

TABLE 5

| FOLIAGE CHARACTERISTICS | | |
|---|---|---|
| Characteristic | 'BOUNTIFUL' (3 Foliate) | 'GRANDEUR' (U.S. Plant Pat. No. 20,459) (3 Foliate) |
| General: | | |
| Color of upper surface | RHS N 137B Green group | RHS N 137A Green group |
| Color of lower surface | RHS 190B Greyed-green group | RHS 190B Greyed-green group |
| Shape in cross section | Flat to slightly concave | Flat to slightly convex |
| Arrangement | Compound | Compound |

TABLE 5-continued

| FOLIAGE CHARACTERISTICS | | |
|---|---|---|
| Characteristic | 'BOUNTIFUL' (3 Foliate) | 'GRANDEUR' (U.S. Plant Pat. No. 20,459) (3 Foliate) |
| Relief between veins (rugosity) | Weak | Strong |
| Glossiness | Weak | Weak |
| Number of leaflets/leaf | Equal 3-5 | Always 3 |
| Terminal Leaflet: | | |
| Length (mm) | 133.3 | 127.5 |
| Width (mm) | 83.6 | 91.6 |
| Length/Width Ratio | 1.6 Longer than broad | 1.4 Longer than broad |
| Size | Medium | Medium to large |
| Shape | Cordate | Cordate |
| Shape of base | Rounded | Cordate |
| Shape of tip | Acuminate | Acuminate |
| Margins | Biserrate | Biserrate |
| Lateral Leaflet: | | |
| Length (mm) | 113.9 | 105.5 |
| Width (mm) | 65.8 | 65.1 |
| Length/Width Ratio | 1.7 Much longer than broad | 1.6 Longer than broad |
| Rachis length (mm) | 37.1 | 36.2 |
| Orientation | Opposite | Opposite |
| Arrangement | Compound | Compound |
| Shape | Ovate | Ovate |
| Overlapping | Free | Touching |
| Shape of the base | Acute | Oblique rounded |
| Shape of the tip | Acuminate | Acuminate |
| Margins | Biserrate | Biserrate |
| Petiole: | | |
| Length (mm) | 63.82 | 59.00 |
| Width (mm) | 3.22 | 3.99 |
| Thorn presence | Yes | Yes |
| Thorn orientation | Erect | Erect |
| Anthocyanin coloration of upper surface | RHS 184B Greyed-purple group | RHS 184C Greyed-purple group |
| Anthocyanin intensity of upper surface | Absent to very weak | Weak |
| Stipule length (mm) | 11.19 | 10.23 |
| Stipule orientation | Erect | Erect to horizontal |

TABLE 6

| FLOWER CHARACTERISTICS | | |
|---|---|---|
| Characteristic | 'BOUNTIFUL' | 'GRANDEUR' (U.S. Plant Pat. No. 20,459) |
| Petal color | 155C White group | 155C White group |
| Flower diameter (mm) | 24.53 | 22.55 |
| Petal Length (mm) | 6.62 | 6.42 |
| Petal width (mm) | 2.89 | 3.11 |
| Petal length/width ratio | 2.29 Much longer than broad | 2.06 Much longer than broad |
| No. petals/flower | 5.4 | 5.2 |
| No. sepals/flower | 5.4 | 5.2 |
| Relative number of pedicel thorns | 25.8 Many | 16.2 Medium |
| Peduncle anthocyanin presence | Present | Present |
| Peduncle anthocyanin coloration | RHS 184A Greyed-purple group | RHS 184A Greyed-purple group |
| Peduncle anthocyanin intensity | Weak | Medium |

TABLE 7

PEST AND DISEASE REACTIONS

| Characteristic | 'BOUNTIFUL' | 'GRANDEUR' (U.S. Plant Pat. No. 20,459) |
|---|---|---|
| Spotted wing drosophila (*Drosophila suzukii*) | Susceptible | Susceptible |
| Two spotted spider mite (*Tetranychus urticae*) | Susceptible | Susceptible |
| Grey fruit mold (*Botrytis cinerae*) | Susceptible | Susceptible |
| Powdery mildew (*Podosphaera aphanis* var. *aphanis*) | Moderately susceptible | Moderately susceptible |

TABLE 7-continued

PEST AND DISEASE REACTIONS

| Characteristic | 'BOUNTIFUL' | 'GRANDEUR' (U.S. Plant Pat. No. 20,459) |
|---|---|---|
| Yellow rust (*Phragmidium rubi-idaei*) | Moderately resistant | Moderately susceptible |

I claim:

1. A new and distinct variety of raspberry plant named 'BOUNTIFUL', as herein described and illustrated by the characteristics set forth above.

* * * * *